United States Patent [19]

Tinti

[11] Patent Number: 4,599,447
[45] Date of Patent: Jul. 8, 1986

[54] PROCESS FOR PREPARING L-NORCARNITINE HYDROCHLORIDE

[75] Inventor: Maria O. Tinti, Rome, Italy

[73] Assignee: Sigma-Tau Industrie Farmaceutiche Riunite S.p.A., Rome, Italy

[21] Appl. No.: 750,689

[22] Filed: Jun. 28, 1985

[30] Foreign Application Priority Data

Jul. 27, 1984 [IT] Italy .................................. 48660 A/84

[51] Int. Cl.$^4$ .......................................... C07C 101/30
[52] U.S. Cl. ................................................... 562/567
[58] Field of Search ................. 562/567; 564/486, 470

[56] References Cited

PUBLICATIONS

Keller, J. Med. Chem. 6, 202–203, (1963).
Stokke, Biochim. Biophys. Acta. 218, pp. 552–554 (1971).

Primary Examiner—Michael L. Shippen
Attorney, Agent, or Firm—Ladas & Parry

[57] ABSTRACT

L-norcarnitine hydrochloride gamma-dimethylamino L-beta-hydroxy butyric acid hydrochloride is prepared by demethylation of L-carnitine chloride with 1,4-diazabicyclo[2,2,2]-octane as demethylating agent.

2 Claims, No Drawings

PROCESS FOR PREPARING L-NORCARNITINE HYDROCHLORIDE

The present invention relates to a process for preparing gamma-dimethylamino L-beta hydroxy butyric acid hydrochloride (L-norcarnitine hydrochloride), having the formula $$(CH_3)_2\overset{+}{N}-CH_2-CH-CH_2-COOH \quad (I)$$
$$\underset{HCl^-}{|} \quad \underset{OH}{|}$$

which clearly shows the structural relationship between (I) and L-carnitine.

Norcarnitine, in addition to being endowed per se with pharmacological properties (see Keller at al, J. Med. Chem. 6, 202, 1963), is a versatile intermediate useful for preparing carnitine and carnitine alkanoyl derivatives (see e.g. the Japanese patent No. 30394, filed Dec. 24, 1959 in the name of Fujisawa Pharmaceutical Co.), which, as known, present several therapeutical utilizations.

There are already known some methods for synthesizing nor-carnitine which present, however, several drawbacks which become particularly serious if an endeavour is made to carry them out on an industrial scale.

For instance, as taught in Biochim. Biophys. Acta 218, 552, (1970) and in J. Label. Compound Radiopham. IX/4, 535, (1982) L-norcarnitine hydrochloride is synthesized as intermediate in the preparation of labelled L-carnitine. According to the method disclosed in these prior art references, L-norcarnitine is obtained in yields varying from 60 to 90% by demethylation of L-carnitine hydrochloride with sodium thiophenate.

It was found, however, that the scaling up of the process from the laboratory scale to the semi-pilot plant scale brings about a dramatic lowering of the yield down to values which are utterly unacceptable from an industrial stand point, while even at the semi-pilot plant scale serious problems originated by the sodium thiophenate toxicity are to be faced.

The object of the present invention is to provide a process for producing L-norcarnitine which does not present the drawbacks of the prior art processes. In particular, via the process of the present invention, which is still based on L-carnitine demethylation, good yields, even on an industrial scale, are achieved, while the demethylating agent utilized does not bring about any toxicity problem.

In accordance with the process of the present invention, L-norcarnitine is prepared via the following scheme:

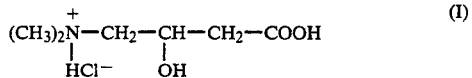
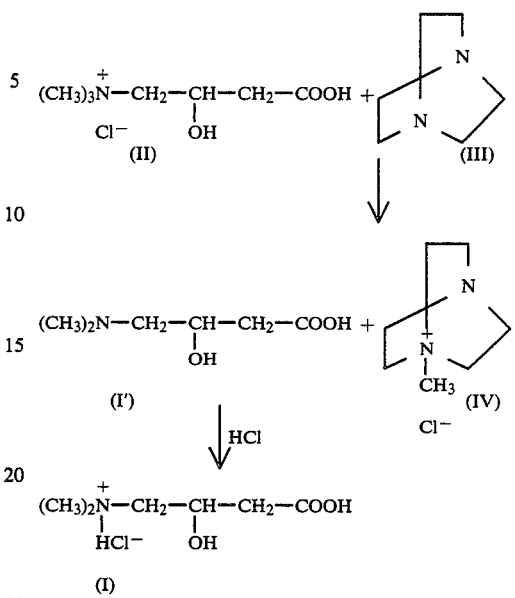

More specifically, the process of the present invention comprises the steps of:

(a) reacting a mixture of L-carnitine chloride (II) and 1,4-diazabicyclo[2,2,2]octane (III) in molar ratio 1:2–1:6 in a high boiling organic solvent, inert to the reaction, at the reflux temperature of the mixture, for about 2–48 hours, thereby obtaining a reaction mixture comprising L-norcarnitine (I'), the N-methyl derivative (IV) of the 1,4 diazabicyclo[2,2,2]octane as side-product, the unreacted excess of (III) and some unreacted (II), if any;

(b) cooling the reaction mixture of step (a) to 4°–10° C. thereby precipitating at least part of the unreacted 1,4 diazabicyclo[2,2,2]octane (III) and of the N-methyl derivative (IV), and filtering off the precipitate;

(c) distilling under vacuum the filtrate of step (b) in order to remove the high boiling solvent, taking up the residue with water, thereby obtaining an aqueous solution;

(d) eluting the solution of the step (c) on a strongly basic ion-exchange resin activated in the OH⁻ form, thereby separating L-norcarnitine (I') which remains on the resin from an eluate comprising the remaining 1,4 diazabicyclo[2,2,2]octane (III), its N-methyl derivative (IV) and the unreacted (II), if any; and (e) eluting the resin of step (d) with 1N–2N hydrochloric acid, thereby obtaining a solution of L-norcarnitine hydrochloride (I).

The high boiling organic solvent of step (a) is selected from benzene, dimethylformamide (DMF) and ethanol, ethanol being preferred. The resin of step (d) is preferably AMBERLITE IRA 402 resin.

The following non-limiting example illustrates the process of the present invention.

EXAMPLE

L-carnitine chloride (1.5 g; 0.008 moles) and 1,4 diazabicyclo[2,2,2]octane (5.25 g; 0.05 moles) were dissolved in 50 cc of DMF at 80° C. The resulting solution was subsequently heated up to 125° C. for 2 hours.

Upon reaction termination, the solution was cooled in an ice bath a 5° C. After about 2 hours the precipitate which formed consisting of the excess diazabicyclo octane and its N-methyl derivative was filtered off. DMF was distilled under vacuum and the residue dissolved in water and eluted on AMBERLITE IRA 402 resin activated in the OH$^{-1}$ form. The eluate having alkaline pH was shown to consist of diazabicyclo octane and its N-methyl derivative; L-norcarnitine which formed was retained on the resin and was eluted therefrom with 2N HCl.

The acid fractions were collected and decolorized with activated carbon and then lyophilized. The residue was twice crystallized from methanol-ethyl acetate giving an oily product (0.7 g; yield 50%);

$[\alpha]_{25} = -17$ (C=1, H$_2$O).

TLC Alumina CHCl$_3$4—EtOH 10—H$_2$O 4

R$_F$=0.3 was consisting with that of a sample of D,L-norcarnitine hydrochloride prepared via a different synthesis method.

NMR D$_2$O δ 4.5 (1H, m,

3.2 (2H, m, N—CH$_2$—); 2.9 (6H, s, (CH$_3$)$_2$N—); 2.4 (2H, d, —CH$_2$COOH).

If desired, in order to obtain a product of higher purity, an aqueous solution of the above-mentioned oily product is eluted on a sulfonic resin, e.g. AMBERLITE IR 120 activated in the H+ form (weight ratio product: resin 1:10). L-norcarnitine is retained on the resin. The resin is eluted with water until a neuter eluate is obtained. The resin is then eluted with a 2% ammonia solution. The alkaline fractions are collected, pooled and lyophilized. L-norcarnitine inner salt is obtained as an oily product. The lyophilizate is crystallized from isopropanol giving a solid product having melting point 113°-115° C., $[\alpha]_D^{25} = -40$ (c=1, H$_2$O).

HPLC: pressure 1000 psi (70.3 kg/cm$^2$); flow rate 1.5 ml/min; columm μ Bondapak NH$_2$; room temperature; eluent KH$_2$PO$_4$ 0.05 M-CH$_3$CN 35-65; UV detector λ=205; chart speed 0.5 cmmin. R$_t$=5.82.

L-norcarnitine inner salt thus obtained is treated with an aqueous solution of HCl (molar ratio 1:1) and the resulting product is lyophilized and crystallized.

What is claimed is:

1. Process for producing L-norcarnitine hydrochloride according to the following reaction scheme

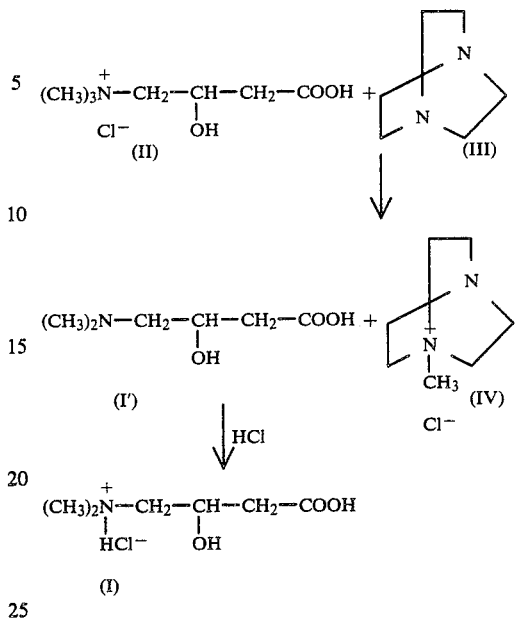

comprising the steps of:
  (a) reacting a mixture of L-carnitine chloride (II) and 1,4-diazabicyclo[2,2,2]octane (III) in molar ratio 1:2-1:6 in a high boiling organic solvent, inert to the reaction, at the reflux temperature of the mixture, for about 2-48 hours, thereby obtaining a reaction mixture comprising L-norcarnitine (I'), the N-methyl derivative (IV) of the 1,4 diazabicyclo[2,2,2]octane as side-product, the unreacted excess of (III) and some unreacted (II), if any;
  (b) cooling the reaction mixture of step (a) to 4°-10° C. thereby precipitating at least part of the unreacted 1,4 diazabicyclo[2,2,2]octane (III) and of the N-methyl derivative (IV), and filtering off the precipitate;
  (c) distilling under vacuum the filtrate of step (b) in order to remove the high boiling solvent, taking up the residue with water, thereby obtaining an aqueous solution;
  (d) eluting the solution of the step (c) on a strongly basic ion-exchange resin activated in the OH$^-$ form, thereby separating L-norcarnitine (I) which remains on the resin from an eluate comprising the remaining 1,4 diazabicyclo[2,2,2]octane (III), its N-methyl derivative (IV) and the unreacted (II), if any; and
  (e) eluting the resin of step (d) with 1N-2N hydrochloric acid, thereby obtaining a solution of L-norcarnitine hydrochloride (I).

2. The process of claim 1 wherein said high boiling organic solvent is selected from benzene, dimethylformamide and ethanol.

* * * * *